(12) United States Patent
Ohtake et al.

(10) Patent No.: US 7,466,151 B2
(45) Date of Patent: Dec. 16, 2008

(54) ELECTRIC-FIELD DISTRIBUTION MEASUREMENT METHOD AND APPARATUS FOR SEMICONDUCTOR DEVICE

(75) Inventors: Hideyuki Ohtake, Kariya (JP); Tomoya Hirosumi, Anjo (JP); Makoto Yoshida, Nagoya (JP); Masayoshi Tonouchi, Mino (JP)

(73) Assignee: Aisin Seiki Kabushiki Kaisha, Aichi-ken (JP)

( * ) Notice: Subject to any disclaimer, the term of this patent is extended or adjusted under 35 U.S.C. 154(b) by 443 days.

(21) Appl. No.: 10/569,796

(22) PCT Filed: Aug. 25, 2004

(86) PCT No.: PCT/JP2004/012613

§ 371 (c)(1),
(2), (4) Date: Feb. 27, 2006

(87) PCT Pub. No.: WO2005/022180

PCT Pub. Date: Mar. 10, 2005

(65) Prior Publication Data

US 2007/0018634 A1    Jan. 25, 2007

(30) Foreign Application Priority Data

Aug. 29, 2003    (JP)    ............................. 2003-307698

(51) Int. Cl.
G01R 31/302    (2006.01)
(52) U.S. Cl. .................................... 324/752; 324/158.1
(58) Field of Classification Search ................. 324/752, 324/750, 751, 158.1; 250/310, 311
See application file for complete search history.

(56) References Cited

U.S. PATENT DOCUMENTS

| 6,011,402 A * | 1/2000 | Kuo et al. ..................... 324/753 |
| 6,057,677 A * | 5/2000 | Wakana et al. ................. 324/96 |
| 6,066,956 A * | 5/2000 | Nikawa ....................... 324/752 |
| 6,566,897 B2 * | 5/2003 | Lo et al. ....................... 324/751 |
| 7,248,062 B1 * | 7/2007 | Samsavar et al. ........... 324/750 |
| 2003/0206027 A1 * | 11/2003 | Nozoe et al. ................. 324/751 |
| 2004/0129879 A1 * | 7/2004 | Furiki et al. ................. 250/310 |

FOREIGN PATENT DOCUMENTS

JP    2000-514549 A    10/2000

OTHER PUBLICATIONS

Kiyomi Sakai, "Terahertz Time-Domain Spectroscopy", Bunko Kenkyu, pp. 261-273, 2001, vol. 50, No. 6.
T. Kiwa, et al.; Backscattered THz Imaging for Extended Abstracts (The 50th Spring Meeting), pp. 1183, Mar. 27, 2003, vol. 3.
David J. Autson, et al., "Electrooptic Generation and Detection of Femtosecond Electrical Transients", IEEE Journal of Quantum Electronics, pp. 184-197, Feb. 19888, vol. 24, No. 2.

* cited by examiner

*Primary Examiner*—Ha Nguyen
*Assistant Examiner*—Richard Isla Rodas
(74) *Attorney, Agent, or Firm*—Sughrue Mion, PLLC

(57) ABSTRACT

It comprises a voltage-application apparatus 2 for applying a predetermined voltage to a semiconductor device 1, and holding it therein; a laser apparatus 3 for generating a laser beam 4 having a predetermined wavelength; an irradiation apparatus 5 for irradiating the laser beam 4 onto the two-dimensional circuit of the semiconductor device 1, which is held in the applied state, so as to scan it two-dimensionally; an electromagnetic-wave detection/conversion apparatus 6 for detecting an electromagnetic wave, which is radiated from the laser-beam irradiation position, and converting the electromagnetic wave into an electric-field signal, which changes temporally; and phase-judgement means 71, to which the temporally-changing electric-field signal output from the detection/conversion apparatus 6 is input, for judging the phase of the electric-field signal.

14 Claims, 8 Drawing Sheets

ELECTRIC-FIELD DISTRIBUTION MEASUREMENT METHOD AND APPARATUS FOR SEMICONDUCTOR DEVICE

TECHNICAL FIELD

The present invention relates to a method and apparatus for measuring the electric field distribution of semiconductor device, such as semiconductor elements and semiconductor integrated circuits, in a non-contact manner. Particularly, it relates to a method and apparatus which irradiates a laser beam in such a state that a voltage is applied to a semiconductor device, and which measures an electric-field distribution from a radiated electromagnetic wave in a non-contact manner. This electric-field measurement method and apparatus can be applied to inspections for defective circuits, such as disconnection in semiconductor devices, defective doping, defective short-circuits between layered films, and the like.

BACKGROUND ART

As a method for measuring the electric-field distribution inside semiconductor device, such as semiconductor integrated circuits and semiconductor elements, in a non-destructive/non-contact manner, a terahertz (THz) electromagnetic-wave imaging method using laser has been known (KIWA Toshihiko and TONOUCHI Masayoshi, "Back-scattered Terahertz Imaging for Fault Isolation in Integrated Circuits," Japan Society of Applied Physics, Springtime Academic Lecture Meeting, Extended Abstracts, the Third Volume, p. 1,183, (Mar. 29, 2003)). This is one in which a THz electromagnetic wave is generated by irradiating a laser beam onto a circuit surface after applying a voltage to the circuit of a semiconductor device and the electric-field strength at the laser irradiation position is measured from the amplitude intensity of the generated electromagnetic wave. However, since this conventional method makes use of the amplitude intensity of the generated electromagnetic wave alone, the difference between the electric-field directions cannot be distinguished and the obtained information is less so that it is insufficient for the inspection or failure diagnosis for semiconductor device. Moreover, the spatial resolution of measurement is prescribed by the diffraction limit of irradiating laser beam, and accordingly there is a problem in view of resolution in order to measure the electric-field distribution of fine semiconductor integrated circuit. Further, the conventional method can measure the electric-field distribution of entire circuit only, and cannot measure the electric-field distribution of specific region, such as the signal channel alone, for instance.

Figure 1:
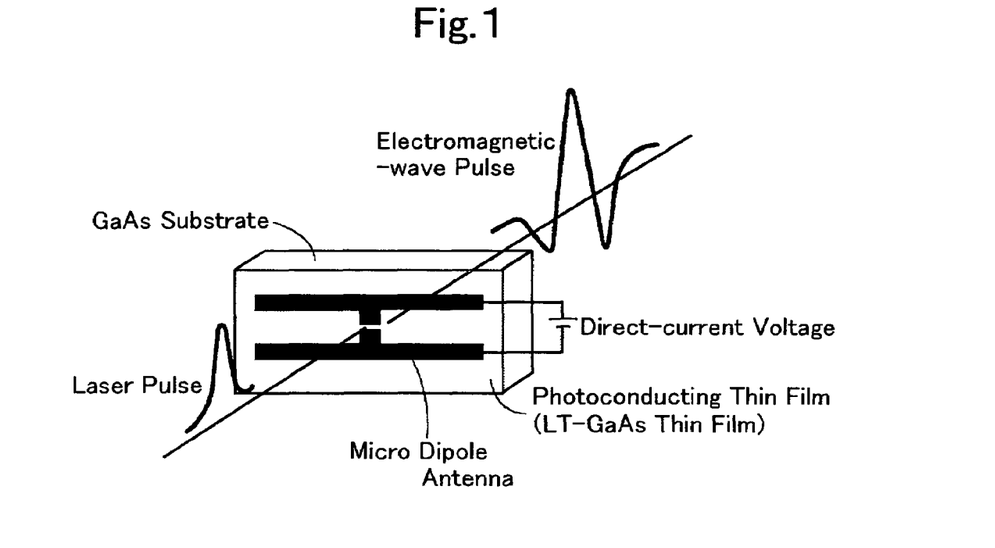
FIG. 1 is a principle diagram on the background art in which an ultra-short optical pulse is irradiated onto a semiconductor switch to radiate a terahertz electromagnetic wave into air.

Moreover, as a technique which is related to the aforementioned prior art, a technique (FIG. 1) has been known, technique in which an ultra-short optical pulse is irradiated onto a semiconductor switch to radiate a terahertz electromagnetic wave into air (D. H. Auston and M. C. Nuss, "ELECTROOPTIC GENERATION AND DETECTION OF FEMTOSECOND ELECTRICAL TRANSIENTS," IEEE JOURNAL OF QUANTUM ELECTRONICS, Vol. 24, pp. 184-197, FEBRUARY 1988.). In FIG. 1, a low-temperature grown (LT) GaAs thin film, which works as a photoconduction film, is grown on a semi-insulative GaAs substrate, and further antenna structures, which are disposed at intervals of 5 μm approximately, are made on it with a gold alloy. In general, an LT-GaAs has been used as a photoconducting thin film in which an electric current flows in an instant only when an optical pulse is irradiated. The gold-alloy portions double as electrodes, and are connected with a direct-current voltage source. The central projections act as a micro dipole antenna, and, when a pulse laser beam is emitted to this gap portion to excite it, the carrier is excited from the valence band to the conduction band by means of light absorption, and the excited carrier relaxes after it is accelerated by the applied voltage. When considering this movement of the carrier an instant electric current, a pulse electromagnetic wave, which is in proportion to the time derivative of this electric current, generates.

As aforementioned, in the prior art, there are such problems that the direction of electric field cannot be distinguished, the spatial resolution of electric-field distribution measurement is low, and the electric-field distribution of specific region cannot be measured.

The present invention is one which has been created anew in order to solve such problematic points. That is, the object of the present invention is to provide an electric-field distribution measurement method and apparatus, which can distinguish the direction of electric field, whose spatial resolution is high, and which can measure the electric field in specific region.

DISCLOSURE OF THE INVENTION

An electric-field distribution measurement method of the present invention for a semiconductor device comprises: a holding step of applying a predetermined voltage to a semiconductor device on which a two-dimensional circuit is formed, and holding the semiconductor device in an applied state; an irradiation step of irradiating a laser beam having a predetermined wavelength onto the two-dimensional circuit of the semiconductor device, which is held in the applied state, so as to scan it two-dimensionally; a detection/conversion step of detecting an electromagnetic wave, which is radiated from a laser-beam irradiation position, and converting it into an electric-field signal, which changes temporally; and a judgement step of judging the phase of the electric-field signal which changes temporally.

Since the phase of the temporally changing waveform of the electric-field signal of the electromagnetic wave, which is radiated from the laser-beam irradiation position, is judged and the direction of the electric field at the laser-beam irradiation position is judged using the fact that the judged phase depends on the direction of the electric field at the laser beam irradiation position, it is possible to distinguish the direction of the electric field.

In the aforementioned method, it can be adapted so that it further comprises a sampling step of sampling the amplitude of an electric field at a predetermined time in said electric-field signal, which changes temporally.

It becomes possible to measure an electric-field strength distribution as well using the fact that the amplitude of the electric field, which is subjected to sampling in the sampling step, is proportional to the strength of the electric field at said laser-beam irradiation position.

Moreover, it is advisable that the predetermined time of the sampling step can comprise a plurality of times; and the sampling step can carry out sampling the amplitude of the electric field at the plurality of times, thereby measuring the electric-field strength distribution at different times.

A time-series electric-field distribution at the identical laser-beam irradiation position can be obtained, and accordingly the identification of doping locations on the substrate of the semiconductor device, and the like, become possible. Further, since the radiated electromagnetic wave is reflected by the interface whose refractive index changes in the depth direction of the substrate so that the reflected wave is radiated from the semiconductor device's surface retardingly, depth-direction information can be obtained by subjecting the amplitude of the electric field of the reflected wave to sampling at different times.

It can be adapted so that the predetermined voltage of said holding step can comprise a voltage, which is modulated with a predetermined frequency; and said detection/conversion step can convert an electromagnetic wave, which is modulated with the modulated frequency, into an electric-field signal, which changes temporally.

It becomes possible to measure the electric field of a circuit portion alone to which the modulated voltage is applied.

It is advisable as well that said laser beam can be adapted to be one which is modulated with a predetermined frequency.

It is possible to measure the electric field distribution of a portion onto which the laser beam is irradiated.

Said irradiation step can irradiate said laser beam onto said two-dimensional circuit so as to scan it two-dimensionally by way of a near-field optical system.

It becomes possible to make the spatial resolution of the electric-field distribution measurement higher than the diffraction limit.

Said predetermined wavelength of said irradiation step can be adapted to being selected so that said laser beam is absorbed by the material of said semiconductor device.

A large number of optical carriers are generated by the irradiated laser beam so that the intensity of the radiated electromagnetic wave increases, and accordingly the S/N of the detection/conversion step improves.

Moreover, an electric-field distribution measurement apparatus of the present invention for solving said assignment is characterized in that it comprises: a voltage-application apparatus for applying a predetermined voltage to a semiconductor device on which a two-dimensional circuit is formed, and holding the semiconductor device in an applied state; a laser apparatus for generating a laser beam having a predetermined wavelength; an irradiation apparatus for irradiating the laser beam onto the two-dimensional circuit of the semiconductor device, which is held in the applied state, so as to scan it two-dimensionally; an electromagnetic-wave detection/conversion apparatus for detecting an electromagnetic wave, which is radiated from the laser-beam irradiation position, and converting the electromagnetic wave into an electric-field signal, which changes temporally; and phase-judgement means, to which the temporally-changing electric-field signal output from the detection/conversion apparatus is input, for judging the phase of the electric-field signal, thereby measuring the electric-field direction distribution using the fact that the phase, which is judged by the phase-judgement means, depends on the electric-field direction at the laser-beam irradiation position.

In the aforementioned apparatus, it can be adapted so that it further comprises electric-field amplitude sampling means, to which said temporally-changing electric-signal output from the electromagnetic-wave detection/conversion apparatus is input, for sampling the amplitude of an electric field at a predetermined time in said electric-field signal and it measures an electric-field strength distribution of said semiconductor device as well using the fact that the amplitude of the electric field, which is subjected to sampling by the sampling means, is proportional to the strength of the electric filed at the laser-beam irradiation position.

Moreover, in the electric-field distribution measurement apparatus of the present invention for a semiconductor device, said electric-field amplitude sampling means can carry out sampling the amplitude of the electric field at a plurality of predetermined times, and can thereby measure the electric-field strength distribution at different times.

Further, said voltage-application apparatus can apply a voltage, which is modulated with a predetermined frequency, to said semiconductor device; and said electromagnetic-wave detection/conversion apparatus can convert an electromagnetic wave alone, which is modulated with the modulated frequency, into an electric-field signal, which changes temporally, and thereby the electric-field distribution of a circuit portion, to which the modulated voltage is applied, can be measured.

It can be adapted so that it comprises modulation means for modulating said laser beam with a predetermined frequency.

In the electric-field distribution measurement apparatus of the present invention for a semiconductor device, said irradiation device can comprise a near-field optical system, and can thereby irradiate said laser beam onto said two-dimensional circuit so as to scan it two-dimensionally by way of the near-field optical system.

Moreover, said laser apparatus can generate a laser beam with a wavelength which is absorbed by the material of said semiconductor device.

BEST MODE FOR CARRYING OUT THE INVENTION

Preferable embodiment modes of the present invention will be hereinafter described with reference to the drawings. Note that, in the respective diagrams, common parts are designated with identical symbols in order to abbreviate duplicate descriptions.

Figure 2:
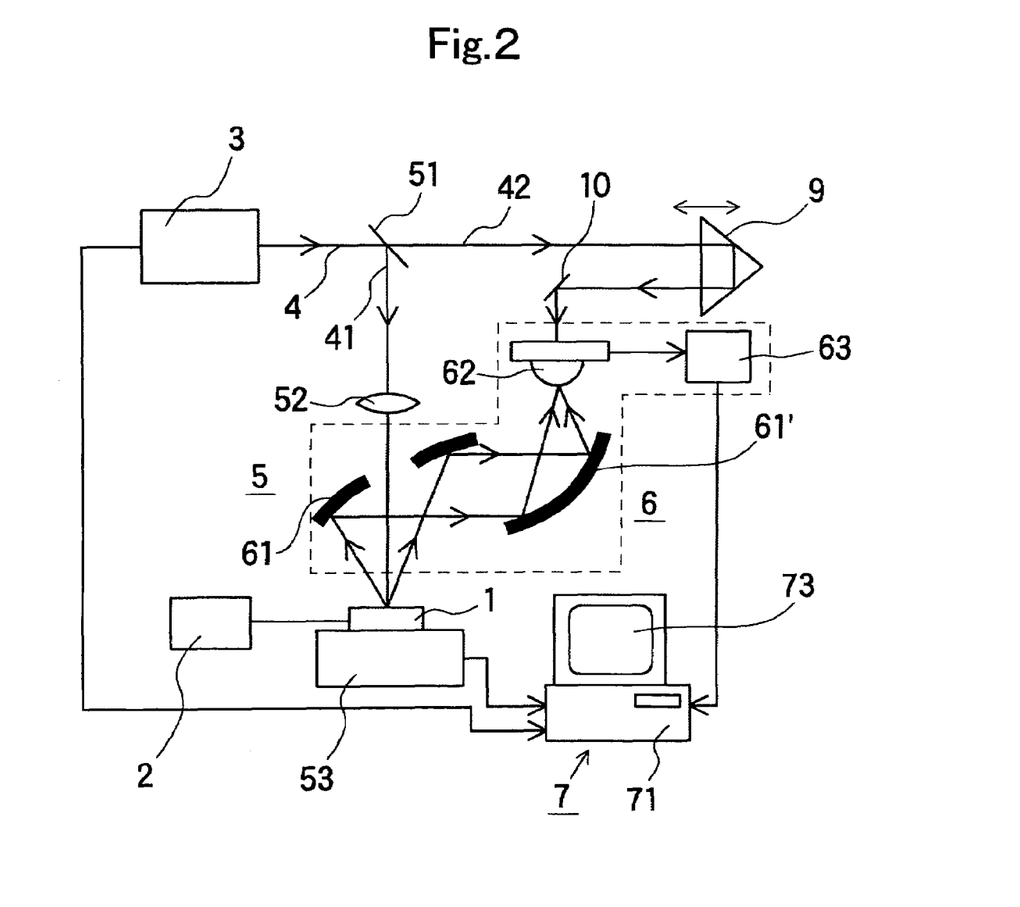
FIG. 2 is not only an outline diagram of an electric-field distribution measurement apparatus of the present invention for a semiconductor device, but also is an outline diagram of an electric-field distribution measurement apparatus A of Example No. 1 for a semiconductor device.

FIG. 2 is an outline diagram of an electric-field distribution measurement apparatus A of Example No. 1 for a semiconductor device, outline diagram which shows an embodiment mode of the present invention. As shown in this diagram, the electric-field distribution measurement apparatus A is equipped with a voltage-application apparatus 2, a laser apparatus 3, an irradiation apparatus 5, an electromagnetic-wave detection/conversion apparatus 6, and phase judgement means 71.

The voltage-application apparatus 2 is an electric power circuit, applies a predetermined voltage to the two-dimensional circuit of a semiconductor 1, a measuring object, and holds it in an applied state. "Applying a predetermined voltage to something and holding it in an applied state" refers to applying a voltage (DC±16 V, for example), which is suitable for the semiconductor device 1, to the electric-power-source line and holding the earth line in a grounded state. Therefore, in this applied state, the circuit portion of the semiconductor device 1, which is connected with the electric-power-source line, becomes a predetermined voltage, and the circuit portion, which is connected with the earth line, becomes being grounded (0 volt, for instance), thereby generating a voltage difference between them. The electric-power-source application apparatus 2 can desirably be capable of supplying ±direct-current voltage and modulated voltage variably. Even when the semiconductor device 1, a measuring object, changes, it is possible to apply a voltage, which is suitable for it. Moreover, it is possible to apply a voltage, which is modulated with a predetermined frequency, to the signal line of the semiconductor device 1, for example.

The laser apparatus 3 generates a laser beam 4. As for the laser apparatus 3, it is possible to use mode-locked laser or fiber laser, and the like, which generates the laser beam 4 of ultra-short optical pulse whose pulse width is femtoseconds, for instance. As for the laser apparatus 3, as far as it is one in which an electromagnetic wave is generated when irradiating the generated laser beam 4 onto the semiconductor device 1, the laser beam 4 is not needed to be an ultra-short optical pulse in particular, it can be two cw-oscillation-semiconductor-laser units, which generate cw laser beams whose oscillation wavelengths are close to each other, for example. The wavelength of the laser beam 4 can desirably be a wavelength which is absorbed by the substrate material of the semiconductor device 1, and it is advisable to select it depending on the substrate material of semiconductor device. That is, when the substrate material is Si, it is desirable to use a laser apparatus, which generates a laser beam whose wavelength is 1,117 nm or less; when it is GaAs, it is desirable to use a laser apparatus, which generates a laser beam whose wavelength is 885 nm or less; and when it is Ge, it is desirable to use a laser apparatus, which generates a laser beam whose wavelength is 1,879 nm or less, respectively. As for the laser apparatus, which generates a laser beam whose wavelength is absorbed by the substrate material of semiconductor device, fiber laser, in which fibers doped with Yb or Er ions are adapted to the amplification medium, is suitable. Further, the wavelength of the laser beam 4 can be a wavelength, which transmits through the package of the semiconductor device 1 and is absorbed by the substrate material of the semiconductor device. It becomes unnecessary to remove the package. Moreover, the mode of the laser beam 4 can preferably be a single mode. The single mode is such that the beam quality is high and it is possible to irradiate it onto the semiconductor device 1 while condensing it to the diffraction limit. Note that, when constituting the package of a material through which the laser beam 4 transmits, it becomes unnecessary to select a wavelength which transmits through the package.

The irradiation apparatus 5 irradiates the laser beam 4 onto the two-dimensional circuit of the semiconductor device 1 so as to scan it two-dimensionally. In the electric-field distribution measurement apparatus A of FIG. 2, the irradiation apparatus 5 comprises a beam splitter 51, which splits the laser beam 4 into two beams, a condenser lens 52, which condenses one of the split laser beams (exciter beam 41) and irradiates it to the semiconductor device 1, and an x-y movement stage 53, on which the semiconductor device 1 is placed and which moves it in the x-direction (direction crossing perpendicularly with the page plane) and in the y-direction (page plane direction), and the semiconductor device 1, which is placed on the stage 53, undergoes the x-y movement by the movement of the x-y movement stage 53, the condensed irradiation spot of the exciter beam 41 by means of the condenser lens 52 scans on the two-dimensional circuit of the semiconductor device 1. By inserting a mirror behind the beam splitter 51, it is possible to adapt so that the exciter beam 41, which is split by the splitter 51, is condensed and irradiated from the rear surface of the semiconductor device 1. By thus doing, since the irradiated exciter beam 41 is not reflected at the metallic films, and the like, which constitute the circuit, it is possible to detect radiated electromagnetic wave efficiently. Moreover, by inserting a near-field optical probe behind the condenser lens 52, it is advisable to adapt the irradiation apparatus 5 to irradiate evernescent wave, which leaks out from the probe's leading end, to the semiconductor device 1. It is possible to minimize the irradiation spot close to the diameter of the probe's leading end, and accordingly it is possible to enhance the spatial resolution of electric-field distribution measurement greater than the diffraction limit of light. Note that, by inserting a galvanometer mirror, for example, behind the condenser lens 52, it is advisable to adapt the irradiation apparatus 5 to irradiate the exciter beam 41, which is split by the beam splitter 51, to the stationary semiconductor device 1 on the stage so as to scan it two-dimensionally.

The electromagnetic-wave detection/conversion apparatus 6 comprises an off-axis parabolic mirror 61, in which a hole through which the irradiated laser beam passes is opened, an off-axis parabolic mirror 61', which is free of hole, an electromagnetic-wave detector 62, and a lock-in amplifier 63. The off-axis parabolic mirrors 61, 61' constitute a condenser optical system, and let electromagnetic wave, which is radiated from the semiconductor device 1, enter the detector 62 efficiently. For the electromagnetic-wave detector 62, it is possible to use photoconductive antennas, or electro-optical crystals, such as ZnTe. To the electromagnetic-wave detector 62, the other beam (trigger beam 42), which is split by the beam splitter 51, enters while being retarded by a retardation line, which is constituted of a corner cube 9 and a mirror 10, and the detector 62 is gated by the trigger beam. It is advisable to install an optical filter, which transmits electromagnetic wave alone, to the electromagnetic-wave detector 62. It is possible to raise the S/N by cutting the background light, such as laser beam, which is reflected at the metallic films of the semiconductor device 1, and the like. When the radiated electromagnetic wave is modulated, it is possible to raise the S/N by synchronizing the lock-in amplifier 63 with the modulated frequency; and at the same, in the case of applying the modulated voltage to the signal line with the voltage-application apparatus 2 as aforementioned, it is possible to convert the electromagnetic wave, which is radiated from the signal line, alone.

Figure 3:
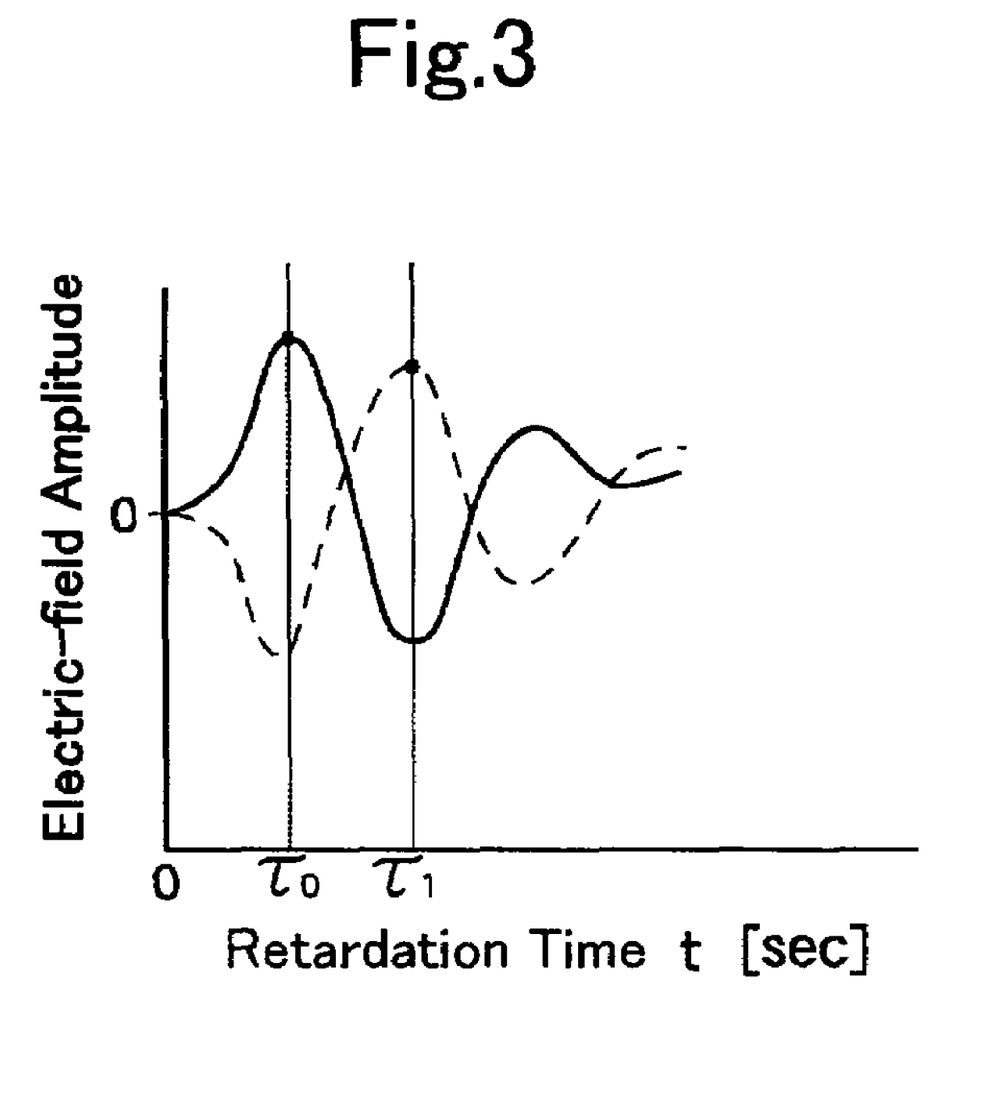
FIG. 3 is a diagram for explaining the electric-field signal of an electromagnetic wave, which is radiated from a semiconductor device, and the sampling time.

The phase judgement means 71 is subjected to the input of temporally-changing signal of the electric field of the electromagnetic wave, temporally-changing signal which is output from the detection/conversion apparatus 6, and judges the phase of the temporally-changing signal. FIG. 3 is one which shows temporal changes of the electric-field amplitude of the electromagnetic wave schematically, and it is judged to be the normal phase in the case of the continuous line and to be the reverse phase in the case of the dotted line. In the electric-field distribution measurement apparatus A, since a personal computer 7 carries out the function, the personal computer 7 comes to have the built-in phase judgement means 71. The personal computer 7 controls the laser apparatus 3 and x-y movement stage 53, judges whether the phase of the temporally-changing signal of the electric field of the electromagnetic wave, temporally-changing signal which is input from the electromagnetic-wave detection/conversion apparatus 6, is the normal phase or reverse phase, and displays the judgement results at positions, which correspond to the semiconductor device 1, on a CRT 73 according to colors.

It is advisable to let the personal computer 7 have the function of electromagnetic-field amplitude sampling means. The electromagnetic-field amplitude sampling means carries out sampling the amplitude of the electric field at predetermined times ($\tau_0$, $\tau_1$ of FIG. 3, for instance) in the temporally-changing signal of the electric field of the electromagnetic wave, the temporally-changing signal which is input from the electromagnetic-wave detection/conversion apparatus 6. The personal computer 7 carries out sampling the amplitude of the electric field at predetermined times in the temporally-changing signal of the electric field of the electromagnetic wave, temporally-changing signal which is input from the electromagnetic-wave detection/conversion apparatus 6, and displays the sampling results at positions, which correspond to the semiconductor device 1, on the CRT 73 according to the colors' shading.

In accordance with an electric-field distribution measurement method of the present invention using the above-described electric-field distribution measurement apparatus A, it comprises: a holding step of holding the semiconductor device 1 in a predetermined voltage application state; an irradiation step of irradiating the laser beam 4 onto the two-dimensional circuit of the semiconductor device 1 so as to scan it two-dimensionally; a detection/conversion step of detecting an electromagnetic wave, which is radiated from the irradiation position, and converting it into an electric-field signal, which changes temporally; and a phase judgement step of judging the phase of the electric-field signal, thereby measuring the direction of the electric field at the irradiation position from the phase of the electric field.

In accordance with an electric-field distribution measurement method of the present invention using the modified mode of the above-described electric-field distribution measurement apparatus A, it further comprises a sampling step of sampling the amplitude of an electric field at a predetermined time in the electric-field signal, thereby measuring an electric-field strength at the irradiation position as well from the amplitude of the electric field.

Moreover, by applying a voltage, which is modulated with a predetermined frequency, to the signal line of the semiconductor device 1, for example, with the voltage-application apparatus 2, and by detecting the electromagnetic wave of the modulated frequency alone with the electromagnetic-wave detection/conversion apparatus 6, it is possible to measure an electric-field distribution of the signal line alone, for instance.

Further, by using a near-field optical probe for the irradiation apparatus 5, it is possible to enhance the spatial resolution of electric-field measurement to the diffraction limit of the laser beam 4 or more.

By letting the personal computer 7 have a phase judgement step and an electric-field amplitude sampling step of sampling the amplitude of an electric field at a plurality of times, it is possible to measure a time-series electric-field direction at an identical position in the semiconductor device 1, and an electric-field strength thereat.

EXAMPLE NO. 1

Above-described FIG. 2 is a constitutional example of an electric-field distribution measurement apparatus A of Example No. 1 of the present invention. That is, it was one in which, by irradiating the laser beam 4 onto the semiconductor device 1 which was in the voltage application state, an electromagnetic wave was generated from the irradiation position; and the radiated electromagnetic wave was detected by the electromagnetic-wave detection/conversion apparatus 6, thereby measuring the phase of the temporally-changing signal of the electric field of the electromagnetic wave.

Figure 4:
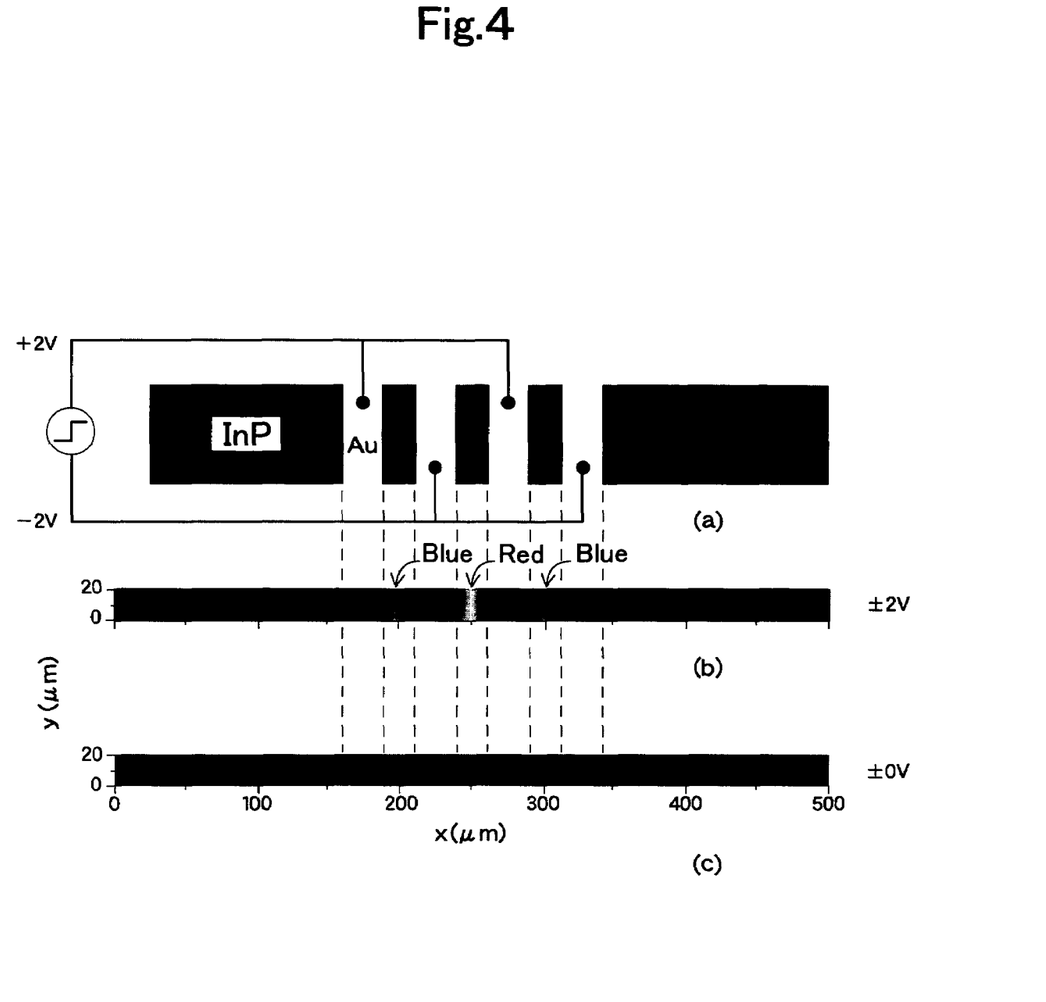
FIG. 4 is a color image for showing an electric-field distribution measurement result of Example No. 1.

The semiconductor device 1 was a test sample on which the test pattern shown in (a) of FIG. 4 was formed. This sample was one in which gold wires of 30 μm width were formed by separating them at intervals of 25 μm on an InP substrate. It was adapted so that +2 V and −2 V direct currents were applied alternately to the gold wires from the voltage-application apparatus 2.

For the laser apparatus 3, mode-locking titanium-sapphire laser was used. From this laser apparatus 3, the laser beam 4, whose wavelength was 790 nm, pulse width was 100 fs, pulse repetition was 82 MHz and average power was 36 mW, was radiated.

The focal length of the condenser lens 52 of the irradiation apparatus 5 was 100 mm, and the irradiation spot diameter of the exciter beam 41 on the test sample 1 was 25 μm.

The laser beam 4 was adapted so that it was modulated to an about 1-KHz frequency and was irradiated to the test sample 1.

As the electromagnetic-wave detector 62 of the electromagnetic-wave detection/conversion apparatus 6, a photoconductive antenna was used.

(b) of FIG. 4 is the result of measuring the phase by irradiating the exciter laser beam 41 onto the test sample 1 while holding it in the voltage application state, and is displayed in colors; in red at the position from which the electromagnetic wave with the normal phase (corresponding to the continuous line of FIG. 3) was radiated; in blue at the positions from which the electromagnetic wave with the reverse phase (corresponding to the dotted line of FIG. 3) was radiated; and in black at the positions from which no electromagnetic wave was radiated. From (a) and (b) of FIG. 4, a leftward electric field was applied to the red region and a rightward electric field was applied to the blue regions, and accordingly it is understood that it was possible to measure the electric-field direction with the electric-field distribution measurement apparatus A of present Example No. 1.

(c) of FIG. 4 is the result of measuring the phase without applying a voltage to the test sample 1, and the entire surface was displayed in one color, black, because there was no electric field so that no electromagnetic wave was radiated.

EXAMPLE NO. 2

Figure 5:
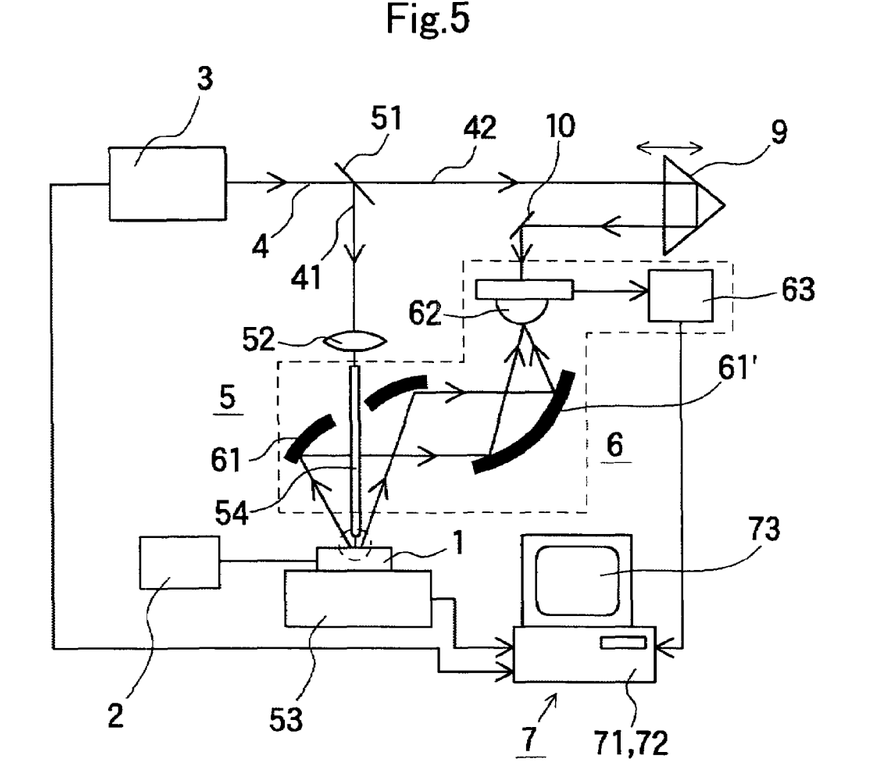
FIG. 5 is an outline diagram of an electric-field distribution measurement apparatus B of Example No. 2 for a semiconductor device.

FIG. 5 is a constitutional example of an electric-field distribution measurement apparatus B of Example No. 2 of the present invention. Except that the irradiation apparatus 5 comprised a near-field optical probe 54, and that the personal computer 7 comprised sampling means 72 for sampling the electric-field amplitude of a temporally-changing signal of an electric field of an electromagnetic wave at a predetermined time, it was the same as Example No. 1.

Figure 6:
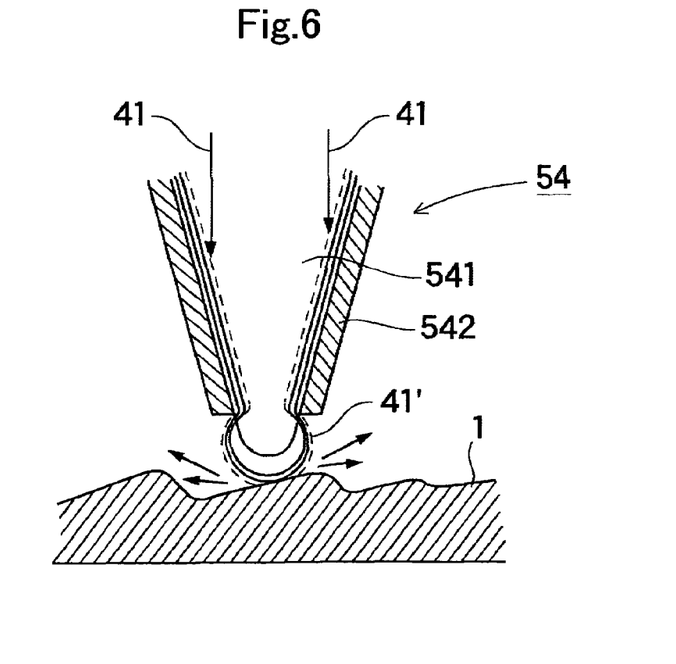
FIG. 6 is an enlarged diagram of the leading end of a near-field optical probe 54 of the electric-field distribution measurement apparatus B of Example No. 2 for a semiconductor device.

FIG. 6 is an enlarged diagram of the leading-end portion of the probe 54, which is surrounded with the circle of FIG. 5. The probe 54 was made of a transparent medium in which the exciter laser beam 41 transmitted, and was covered with a metallic film 542 other than the entrance end and emission end. The diameter of the emission end's opening portion, which was not covered with the metallic film 542, was 0.2 μm; and an evernescent wave 41' of the exciter beam 41 leaked out through this opening portion, and was irradiated onto the semiconductor device 1.

Figure 7:
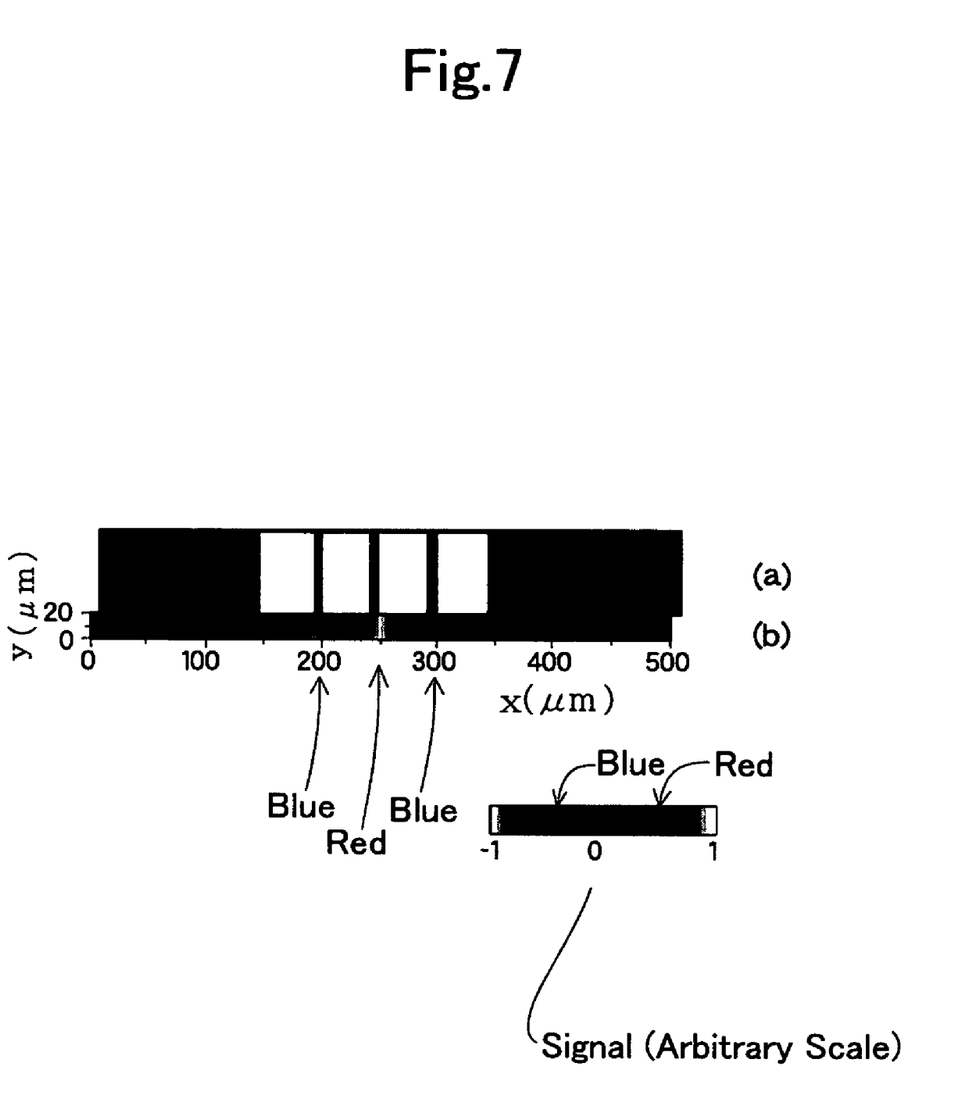
FIG. 7 is a color image for showing an electric-field distribution measurement result of Example No. 2.

The semiconductor device 1 of Example No. 2 was a test sample like Example No. 1 as well, and had dimensions shown in FIG. 7. That is, the width of a gold wire was 6 μm, and the interval between a gold wire and a gold wire was 1 μm.

(b) of FIG. 7 is the result of measuring the phase and the amplitude of electric field by irradiating the evernescent wave 41' of the exciter laser beam 41 onto the test sample 1 while holding it in the voltage application state, and the phase is distinguished in red and blue and at the same time the magnitude of the amplitude is displayed in the concentration of colors. From this, it is understood that the electric-field direction and electric-field strength were measured even when the intervals between the gold wires were 1 μm. That is, by irradiating the exciter beam 41 via the near-field optical prove 54, 1-μm spatial resolution was achieved.

EXAMPLE NO. 3

Figure 8:
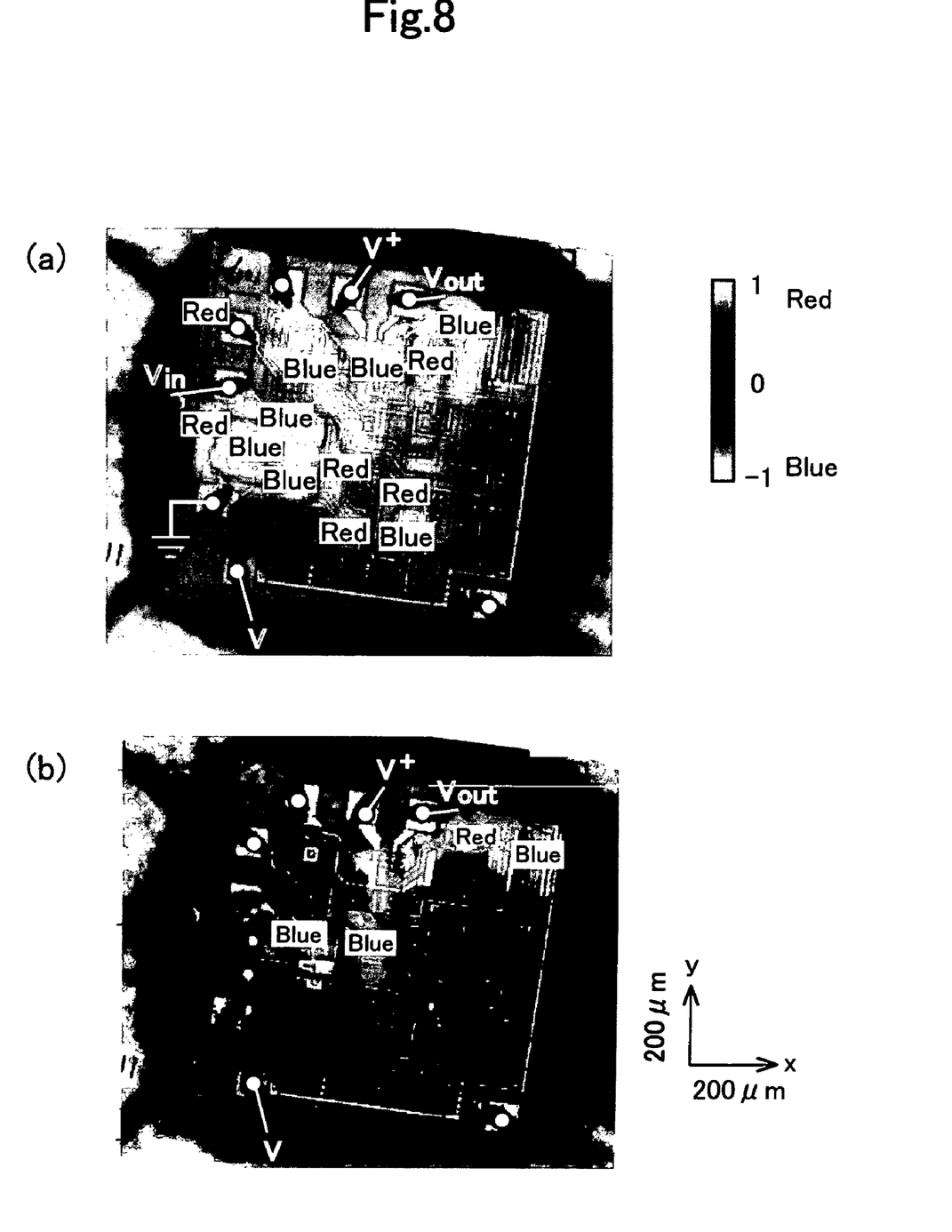
FIG. 8 is a color image for showing an electric-field distribution measurement result of Example No. 3.

FIG. 8 is the result of measuring an electric-field distribution, using an operational amplifier (LM301AH: National Semiconductor) as the semiconductor device 1 of the electric-field measurement apparatus A of Example No. 1 of the present invention. FIG. 8 (a) is the result of measuring the electric-field distribution in such a state that the laser beam 4, which was modulated by modulating the laser apparatus 3 with 2-KHz frequency, was generated and ±16 V (direct current) was supplied to the power-source line of the operational amplifier 1 and −10 V (direct current) was supplied to the signal line thereof with the voltage application apparatus 2, respectively, and it was possible to know the entire electric-field distribution of the operational amplifier 1. FIG. 8 (b) is the result of measuring the electric-field distribution in such a state that ±10 V modulated voltage, which was modulated with 2 KHz, was supplied to the signal line of the operational amplifier 1 with the voltage-application apparatus 2, instead of modulating the laser apparatus 3, and it was possible to know the electric-field distribution of the signal line alone.

EXAMPLE NO. 4

Figure 9:
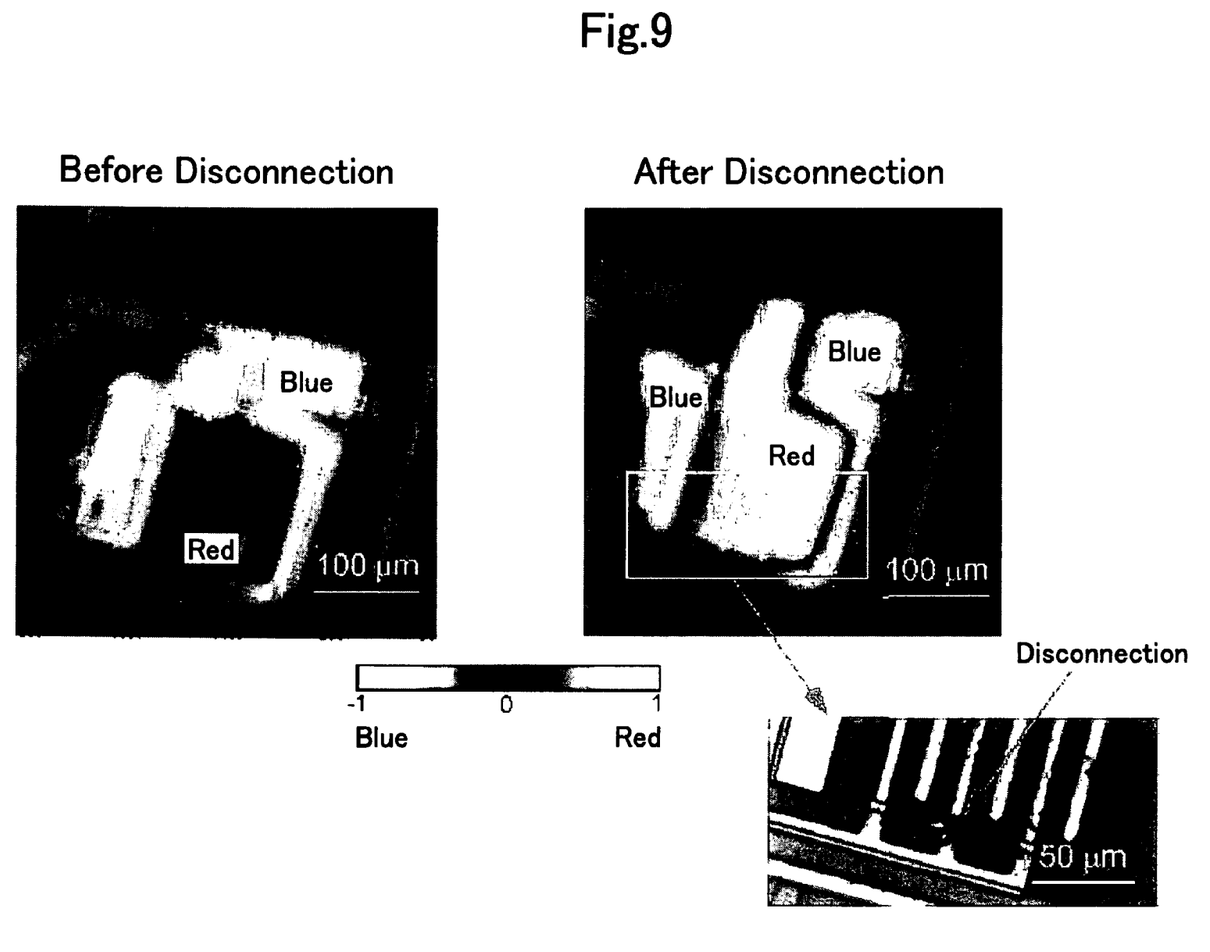
FIG. 9 is a color image for showing an electric-field distribution measurement result of Example No. 4.

FIG. 9 is the result of measuring the electric-field distribution of the operational amplifier 1, which was used in Example No. 3, with high resolution, using the electric-field measurement apparatus B of Example No. 2. That is, the upper left-side diagram is the result of measuring the electric-field distribution in such a state that the laser beam 4, which was modulated by modulating the laser apparatus 3 with 2-KHz frequency, was generated and ±16 V (direct current) was supplied to the power-source line of the operational amplifier 1 and −10 V (direct current) was supplied to the signal line thereof with the voltage application apparatus 2, respectively. Meanwhile, the upper right-side diagram of FIG. 9 is the result of measuring the electric-field distribution after part of the circuit was disconnected intentionally as shown in the right bottom, and it is understood that the electric-field distribution was changed greatly by the disconnection and it is shown that the present invention could be applied to the inspection for the disconnection of semiconductor device, and the like.

EXAMPLE NO. 5

Figure 10:
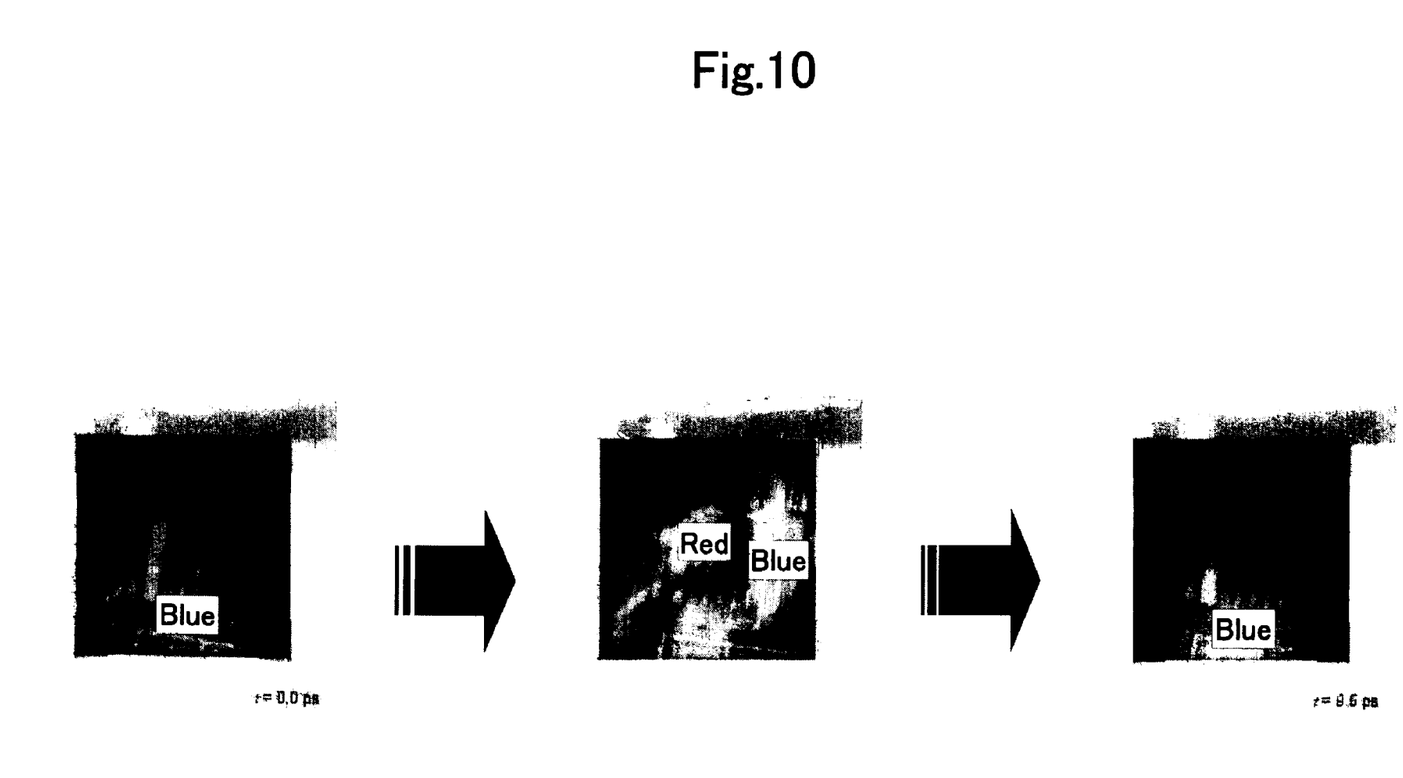
FIG. 10 is a color image for showing an electric-field distribution measurement result of Example No. 5.

FIG. 10 is the result of measuring the electric-field distribution of the operational amplifier 1 of Example No. 3 for the temporal change of the electric-field distribution in a specific area of the operational amplifier 1, using the electric-field measurement apparatus B of Example No. 2. The left diagram of FIG. 10 is the electric-field distribution at a time ($\tau$=0 ps) when the amplitude of the electric field first became the peak value; the central diagram is that at $\tau$=5 ps; and the right diagram is the electric-field distribution at $\tau$=9.5 ps. Although the operational amplifier 1's the voltage applying/holding state by the voltage-application apparatus 2 was constant, the electric-field distribution changed with time series, it is believed to result from the fact that it came under influence other than the optical carrier, which was generated by the irradiation of the exciter beam 41, the influence of doping level's inhomogeneity, for instance. Therefore, it was shown that it was possible to measure the temporal change of the electric-filed distribution by sampling the amplitude of the electric field at different times and accordingly it was possible to evaluate the doping level's inhomogeneity, and so forth.

INDUSTRIAL APPLICABILITY

The electric-field distribution measurement method and apparatus of the present invention for a semiconductor can be utilized not only in the electric-field distribution measurement at the development stages of semiconductor devices, but also can be utilized in the inspection for the disconnection, defect, operational failure, and the like, at the product production stages of semiconductor devices.

The invention claimed is:

1. An electric-field distribution measurement method for a semiconductor device, comprising:
   a holding step of applying a predetermined voltage to a semiconductor device on which a two-dimensional circuit is formed, and holding the semiconductor device in an applied state;
   an irradiation step of irradiating a laser beam having a predetermined wavelength onto the two-dimensional circuit of the semiconductor device, which is held in the applied state, so as to scan it two-dimensionally;
   a detection/conversion step of detecting an electromagnetic wave, which is radiated from a laser-beam irradiation position on said semiconductor device to which said laser beam is irradiated, and converting the electromagnetic wave into an electric-field signal, which changes temporally; and
   a judgement step of judging the phase of the electric-field signal which changes temporally, and the electric-field distribution measurement method for the semiconductor device,
   wherein the electric-field direction distribution of said semiconductor device is measured using the fact that the phase, which is judged in said judgement step, depends on the electric-field direction at the laser-beam irradiation position.

2. The electric-field distribution measurement method for a semiconductor device as set forth in claim 1, comprising a sampling step of sampling the amplitude of an electric field at a predetermined time in said electric-field signal, which changes temporally, and an electric-field strength distribution is measured as well using the fact that the amplitude of the electric field, which is subjected to sampling in the sampling step, is proportional to the strength of the electric filed at said laser-beam irradiation position.

3. The electric-field distribution measurement method for a semiconductor device as set forth in claim 2, wherein the predetermined time of the sampling step comprises a plurality of times; and the sampling step carries out sampling the amplitude of the electric field at the plurality of times, thereby measuring the electric-field strength distribution at different times.

4. The electric-field distribution measurement method for a semiconductor device as set forth in claim 1, wherein said laser beam is one which is modulated with a predetermined frequency.

5. The electric-field distribution measurement method for a semiconductor device as set forth in claim 1, wherein the predetermined voltage of said holding step comprises a voltage, which is modulated with a predetermined frequency; and said detection/conversion step converts an electromagnetic wave, which is modulated with the modulated frequency, into an electric-field signal, which changes temporally, thereby measuring the electric-field distribution of a circuit portion to which the modulated voltage is applied.

6. The electric-field distribution measurement method for a semiconductor device as set forth in claim 1, wherein said irradiation step irradiates said laser beam onto said two-dimensional circuit so as to scan it two-dimensionally by way of a near-field optical system.

7. The electric-field distribution measurement method for a semiconductor device as set forth in claim 1, wherein said predetermined wavelength of said irradiation step is selected so that said laser beam is absorbed by the material of said semiconductor device.

8. An electric-field distribution measurement apparatus for a semiconductor device, comprising:
a voltage-application apparatus for applying a predetermined voltage to a semiconductor device on which a two-dimensional circuit is formed, and holding the semiconductor device in an applied state;
a laser apparatus for generating a laser beam having a predetermined wavelength;
an irradiation apparatus for irradiating the laser beam onto the two-dimensional circuit of the semiconductor device, which is held in the applied state, so as to scan it two-dimensionally;
an electromagnetic-wave detection/conversion apparatus for detecting an electromagnetic wave which is radiated from a laser-beam irradiation position on said semiconductor device to which said laser beam is irradiated, and converting the electromagnetic wave into an electric-field signal, which changes temporally; and
phase-judgement means, to which the temporally-changing electric-field signal output from the detection/conversion apparatus is input, for judging the phase of the electric-field signal, and
wherein the electric-field distribution measurement apparatus for the semiconductor device it measures the electric-field direction distribution of said semiconductor device using the fact that the phase, which is judged by the phase-judgement means, depends on the electric-field direction at the laser-beam irradiation position.

9. The electric-field distribution measurement apparatus for a semiconductor device as set forth in claim 8, further comprising electric-field amplitude sampling means, to which said temporally-changing electric-signal output from the electromagnetic-wave detection/conversion apparatus is input, for sampling the amplitude of an electric field at a predetermined time in said electric-field signal and it measures an electric-field strength distribution of said semiconductor device as well using the fact that the amplitude of the electric field, which is subjected to sampling by the sampling means, is proportional to the strength of the electric filed at the laser-beam irradiation position.

10. The electric-field distribution measurement apparatus for a semiconductor device as set forth in claim 9 wherein said electric-field amplitude sampling means carries out sampling the amplitude of the electric field at a plurality of predetermined times, and thereby measures the electric-field strength distribution at different times.

11. The electric-field distribution measurement apparatus for a semiconductor device as set forth in claim 8, comprising modulation means for modulating said laser beam with a predetermined frequency.

12. The electric-field distribution measurement apparatus for a semiconductor device as set forth in claim 8, wherein said voltage-application apparatus applies a voltage, which is modulated with a predetermined frequency, to said semiconductor device; and said electromagnetic-wave detection/conversion apparatus converts an electromagnetic wave alone, which is modulated with the modulated frequency, into an electric-field signal, which changes temporally, and thereby measures the electric-field distribution of a circuit portion to which the modulated voltage is applied.

13. The electric-field distribution measurement method for a semiconductor device as set forth in claim 8, wherein said irradiation apparatus comprises a near-field optical system, and thereby irradiates said laser beam onto said two-dimensional circuit so as to scan it two-dimensionally by way of the near-field optical system.

14. The electric-field distribution measurement apparatus for a semiconductor device as set forth in claim 8, wherein said laser apparatus generates a laser beam with a wavelength which is absorbed by the material of said semiconductor device.

* * * * *